(12) United States Patent
Chuvashova et al.

(10) Patent No.: US 12,102,806 B2
(45) Date of Patent: *Oct. 1, 2024

(54) ACTUATION MECHANISM

(71) Applicant: SHL Medical AG, Zug (CH)

(72) Inventors: Natalia Chuvashova, Nacka (SE); Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 280 days.

This patent is subject to a terminal disclaimer.

(21) Appl. No.: 17/658,020

(22) Filed: Apr. 5, 2022

(65) Prior Publication Data

US 2022/0233780 A1 Jul. 28, 2022

Related U.S. Application Data

(63) Continuation of application No. 16/301,341, filed as application No. PCT/EP2017/060966 on May 9, 2017, now Pat. No. 11,331,435.

(51) Int. Cl.
*A61M 5/00* (2006.01)
*A61M 5/315* (2006.01)

(52) U.S. Cl.
CPC .... *A61M 5/31556* (2013.01); *A61M 5/31505* (2013.01); *A61M 5/31541* (2013.01);
(Continued)

(58) Field of Classification Search
CPC ............ A61M 5/31541; A61M 5/3155; A61M 5/31593; A61M 5/31585
See application file for complete search history.

(56) References Cited

U.S. PATENT DOCUMENTS

2009/0137964 A1 5/2009 Enggaard
2009/0299297 A1 12/2009 Moeller
(Continued)

FOREIGN PATENT DOCUMENTS

CN 102458535 A 5/2012
CN 104507518 A 4/2015
(Continued)

OTHER PUBLICATIONS

International Search Report and Written Opinion for International Application No. PCT/EP2017/060966, mailed Jul. 17, 2017.

*Primary Examiner* — Nathan R Price
*Assistant Examiner* — Tania Ismail
(74) *Attorney, Agent, or Firm* — McDonnell Boehnen Hulbert & Berghoff LLP

(57) ABSTRACT

An actuation mechanism is presented for a medicament delivery device having a plunger rod arranged to act on a stopper of a medicament container, an actuator arranged slidable and connected to the plunger rod for acting on the stopper when said actuator is operated by displacing it in a longitudinal direction of the actuation mechanism, and an activator for activating the actuation mechanism and for setting a dose. The activator having a generally tubular activator sleeve provided with a spirally extending groove on an outer surface, the groove arranged with a length corresponding to the total amount of medicament to be delivered in a number of doses contained in said medicament container, where the groove is provided with an end wall, a stop ring arranged coaxial with said activator sleeve. The activator sleeve arranged with a follower positioned in the groove and the follower arranged to abut the end wall when the total amount has been delivered.

20 Claims, 18 Drawing Sheets

(52) U.S. Cl.
CPC ...... *A61M 5/3155* (2013.01); *A61M 5/31565* (2013.01); *A61M 5/3158* (2013.01); *A61M 5/31581* (2013.01); *A61M 5/31593* (2013.01); *A61M 5/31585* (2013.01)

(56) References Cited

U.S. PATENT DOCUMENTS

| | | |
|---|---|---|
| 2012/0283647 A1 | 11/2012 | Cronenberg |
| 2012/0283659 A1 | 11/2012 | Kouyoumijian |
| 2012/0310206 A1 | 12/2012 | Kouyoumijian |
| 2016/0067412 A1 | 3/2016 | Bayer |

FOREIGN PATENT DOCUMENTS

| | | |
|---|---|---|
| CN | 104519929 A | 4/2015 |
| CN | 105102022 A | 11/2015 |
| CN | 105263546 A | 1/2016 |
| CN | 105492044 A | 4/2016 |
| EP | 3006064 A1 | 4/2016 |
| TW | 522138 B | 2/2016 |
| TW | 526230 B | 3/2016 |
| TW | 527604 B | 4/2016 |
| WO | 2004/078242 A1 | 9/2004 |
| WO | 2010/8139645 A1 | 12/2010 |
| WO | 2014/005807 A1 | 1/2014 |
| WO | 2014/005808 A1 | 1/2014 |
| WO | 2014/033197 A1 | 3/2014 |
| WO | 2014/166892 A1 | 10/2014 |
| WO | 2014/166922 A2 | 10/2014 |
| WO | 2016/001304 A1 | 1/2016 |
| WO | 2016/055626 A1 | 4/2016 |

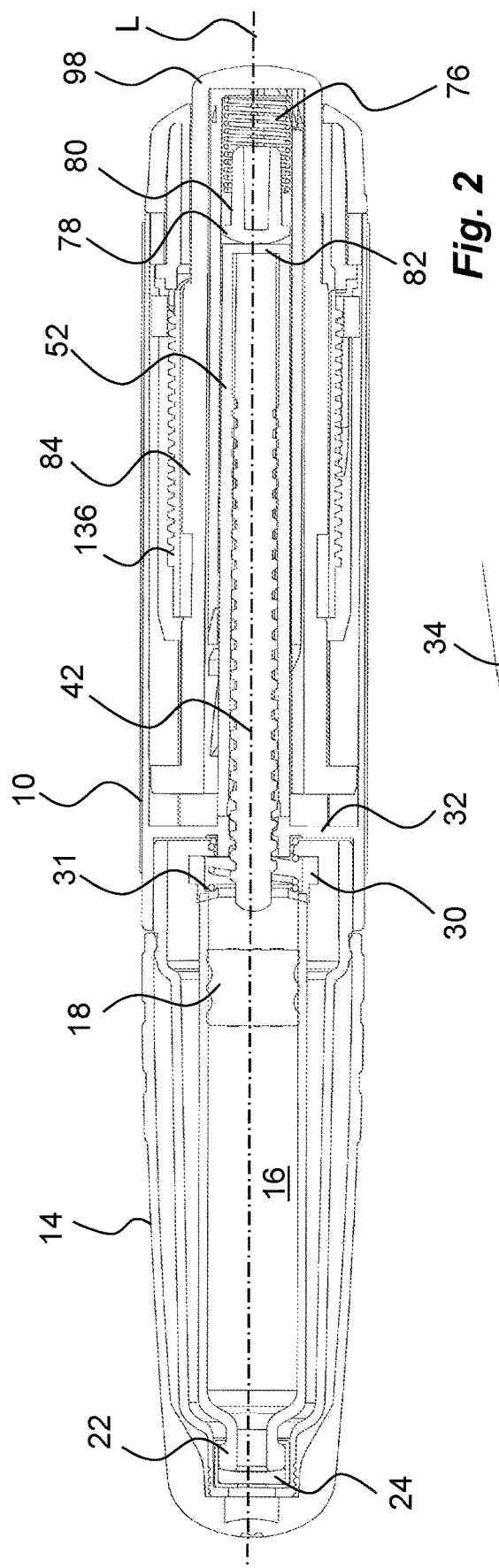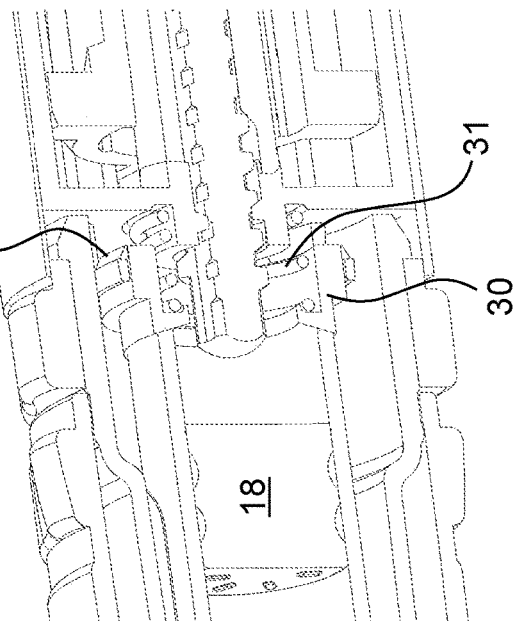
Fig. 2
Fig. 3

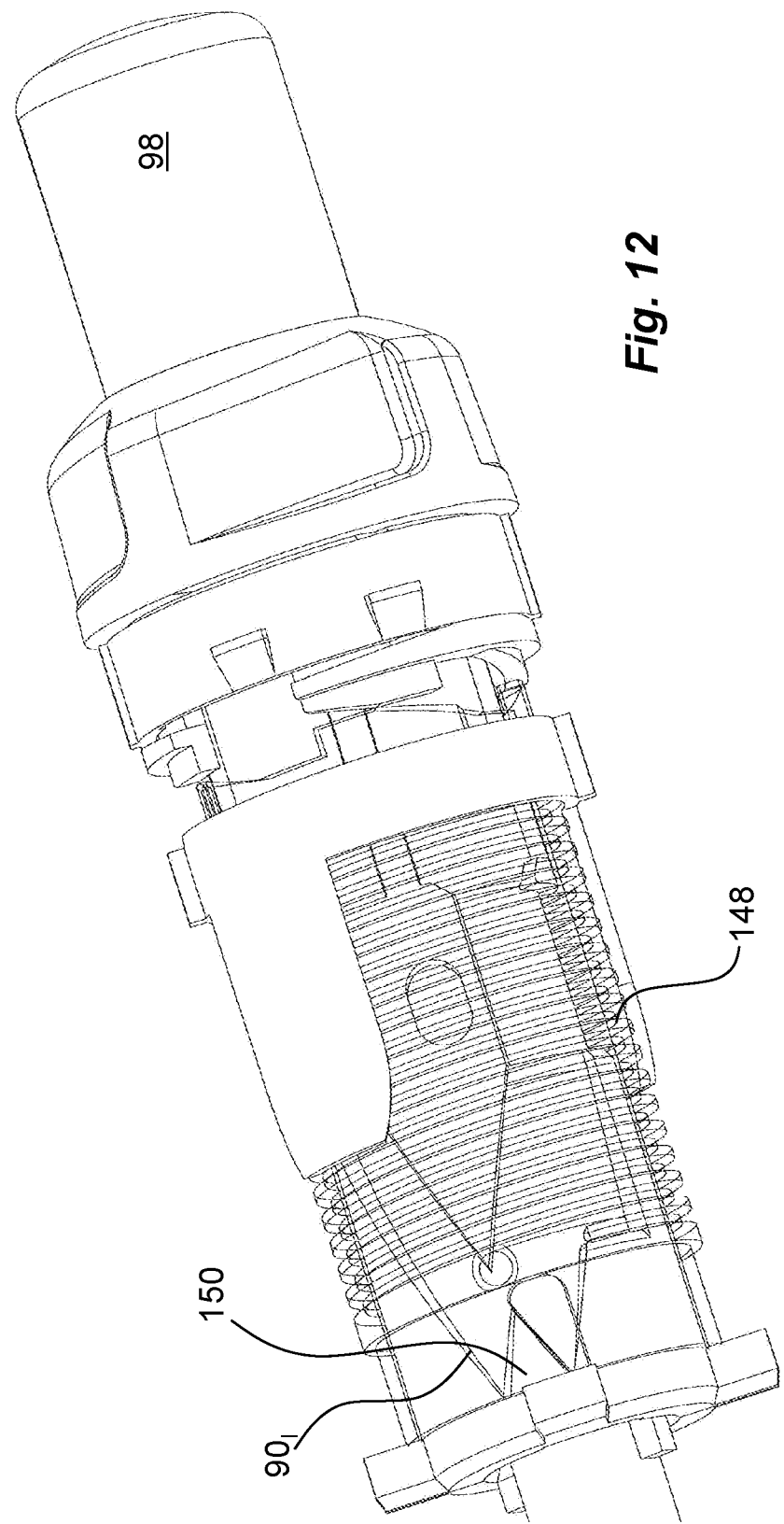

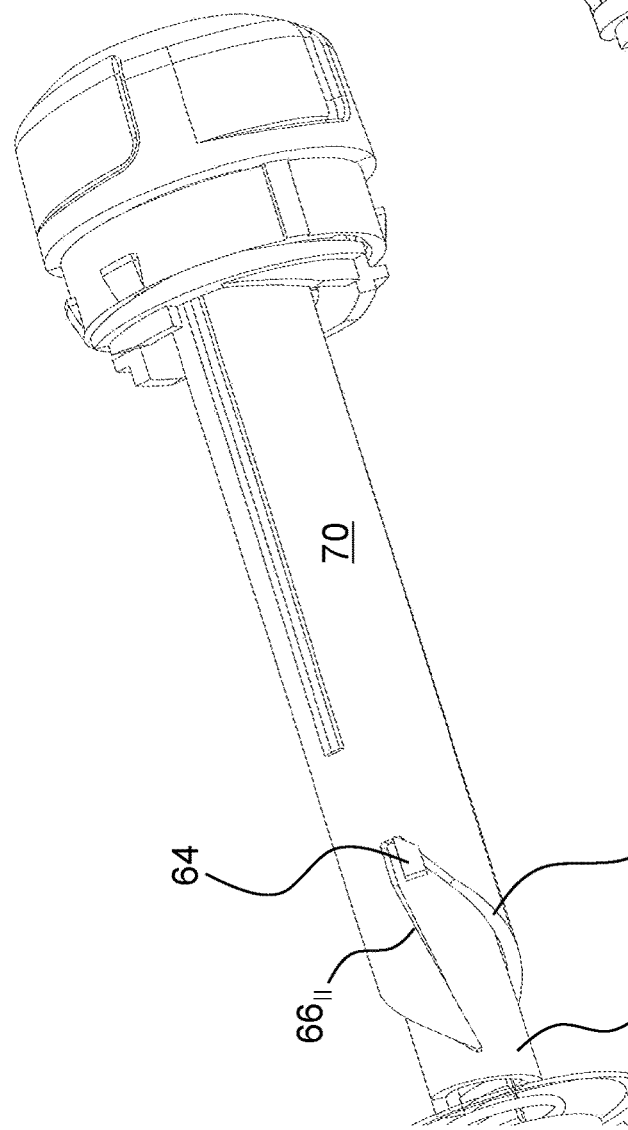
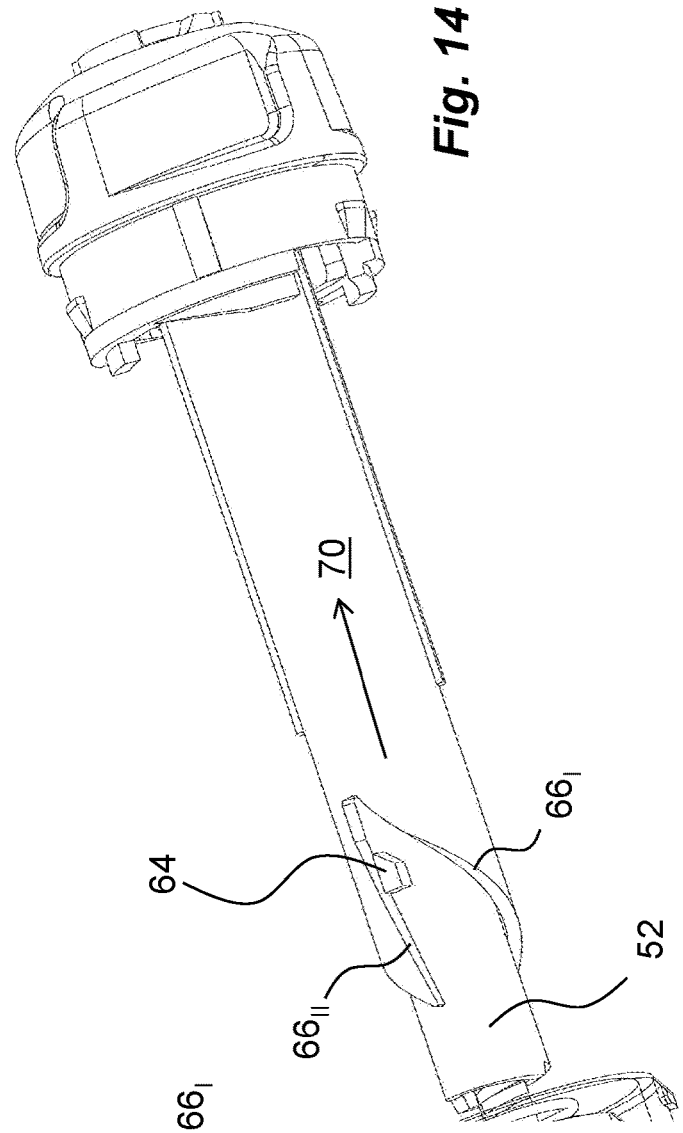

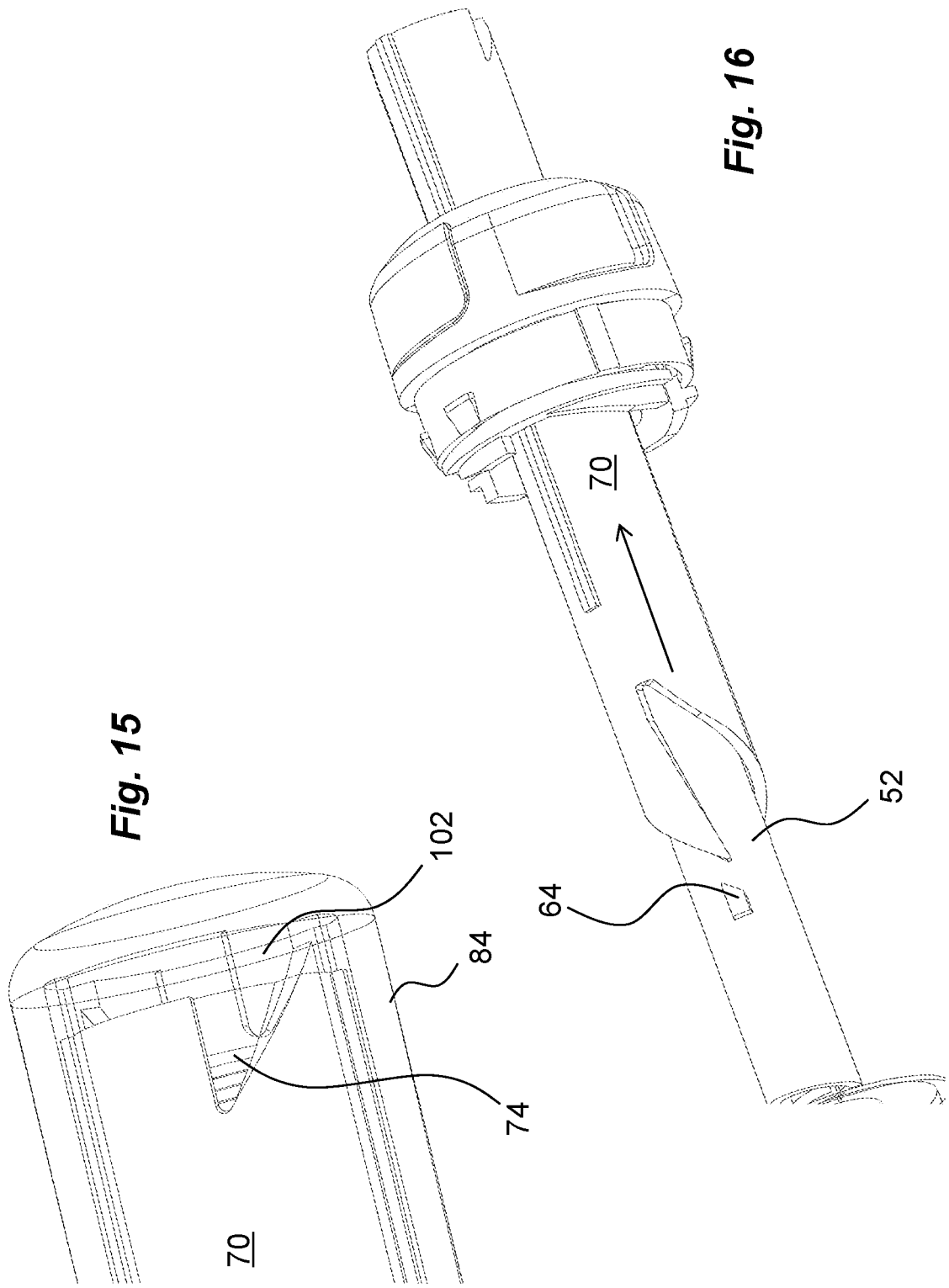

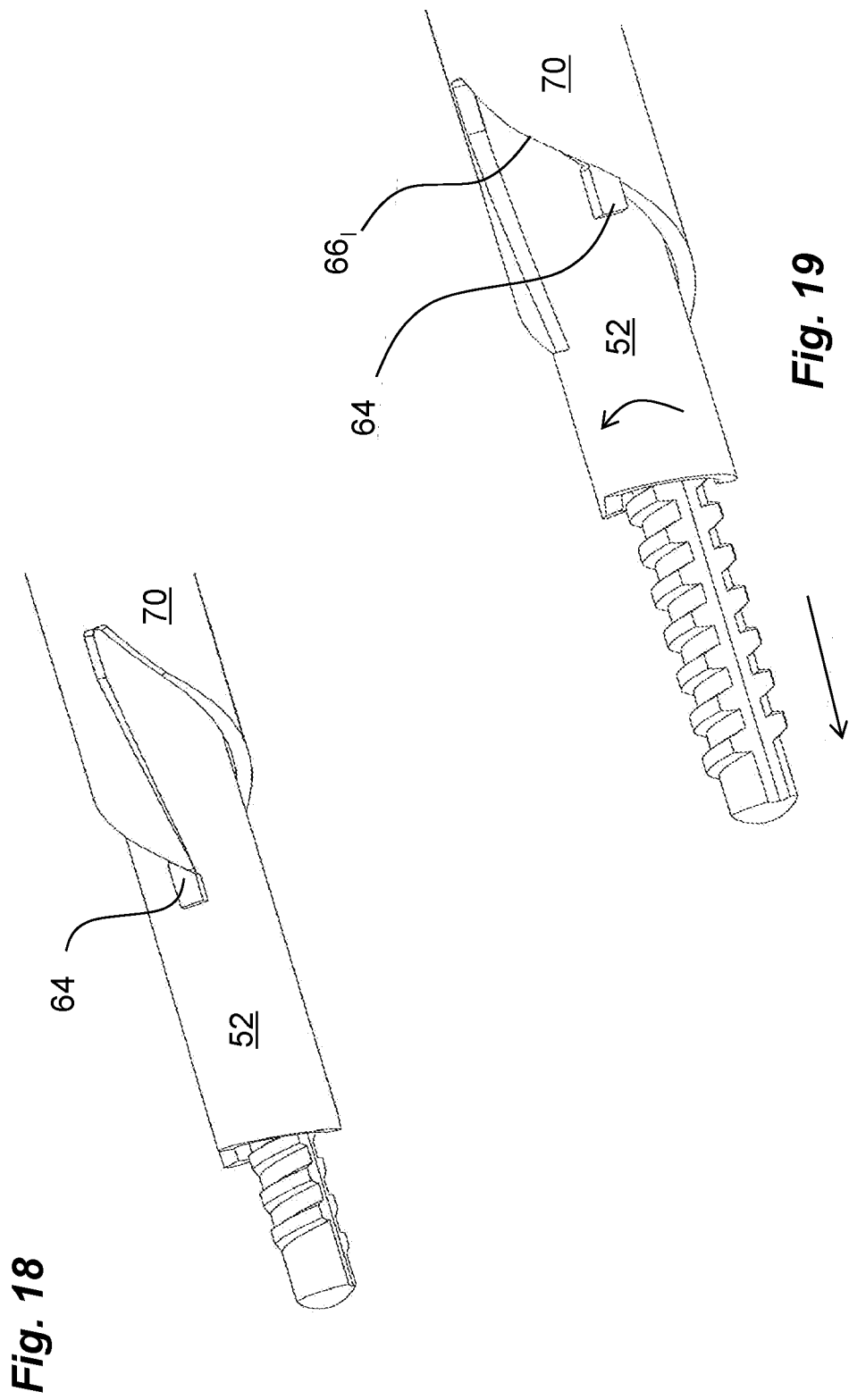

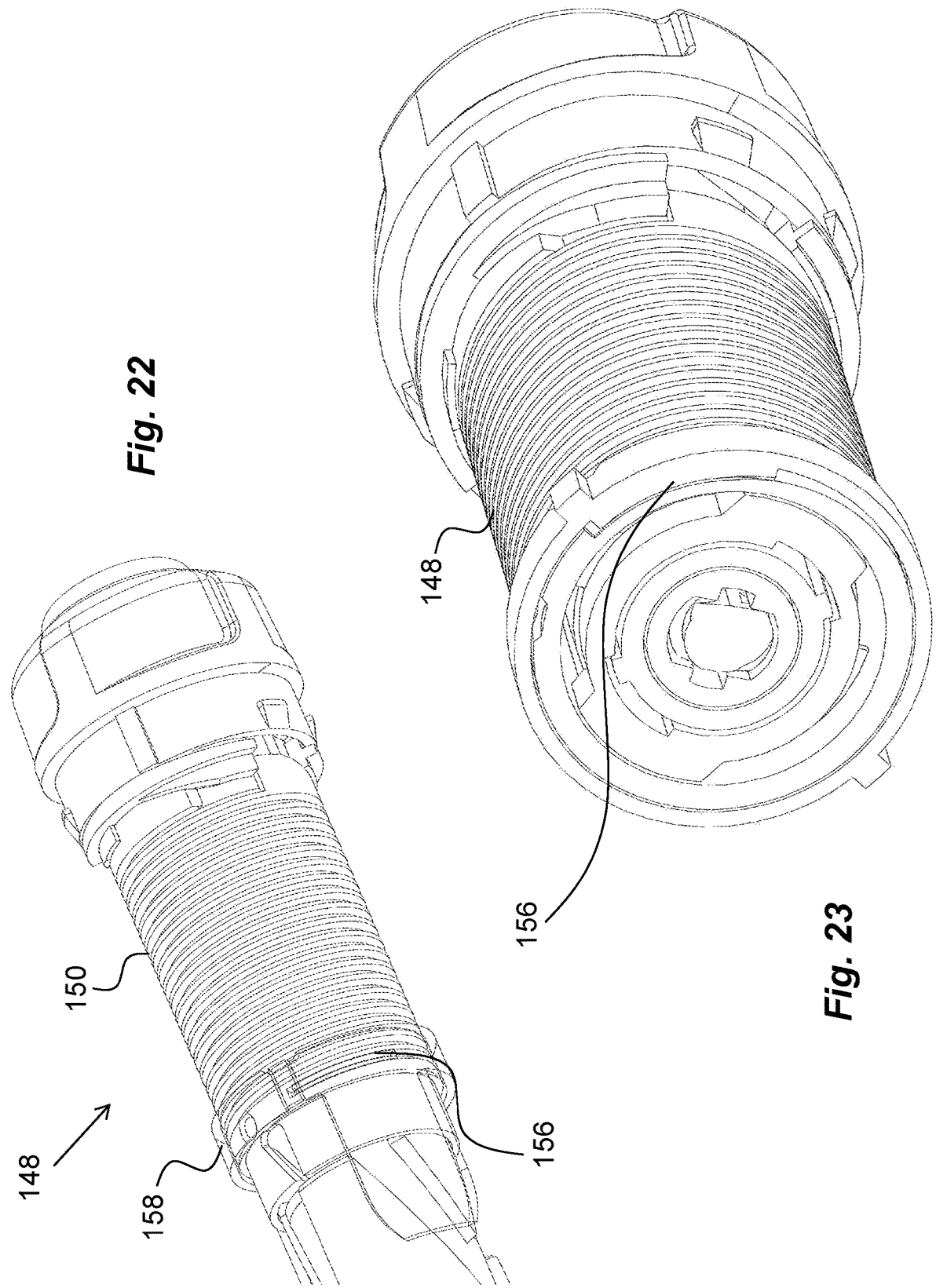

ACTUATION MECHANISM

CROSS REFERENCE TO RELATED APPLICATIONS

The present application is a continuation of U.S. patent application Ser. No. 16/301,341 filed Nov. 13, 2018, which is a U.S. National Phase Application pursuant to 35 U.S.C. § 371 of International Application No. PCT/EP2017/060966 filed May 9, 2017, which claims priority to Swedish Patent Application No. 1650741-0 filed May 27, 2016. The entire disclosure contents of these applications are herewith incorporated by reference into the present application.

TECHNICAL AREA

The present disclosure relates to an actuation mechanism for a medicament delivery device and in particular a so called pen injector provided with a number of specific features.

BACKGROUND

Many injectors on the market, especially pen-injectors, are provided with a functionality to allow multiple doses to be given from a medicament container. In many instances the dose quantity is fixed and is set just before a dose is to be delivered. Thus, a manual dose setting sequence is first performed and then a manual dose delivery sequence is performed.

Document US 2009/0137964 discloses such a medicament delivery device having a dose setting member that is turned. The dose setting member is connected to a dose indicator barrel having a set of numerals that are visible through a window in a housing part. A nut member provided with a thread segment is arranged between the dose setting member and an internal thread on the housing. The length of the internal thread corresponds to the length that the piston rod has to travel in order to empty the medicament container and a stop on the thread segment engages an end wall of the internal thread when the medicament container is empty which thereby prevents the user for setting a dose larger than the remaining content of the medicament container.

SUMMARY

The aim of the present disclosure is to provide a reliable and simple solution of preventing setting of doses of medicament that are larger than the remaining quantity of a medicament container.

This aim is solved with a drive mechanism comprising the features of the independent patent claim. Preferable embodiments of the disclosure form the subject of the dependent patent claims.

According to a main aspect of the disclosure, it may comprise an actuation mechanism to be used with a medicament delivery device. The actuation mechanism may comprise a plunger rod arranged to act on a stopper of a medicament container; an actuator arranged slidable and connected to the plunger rod for acting on the stopper when said actuator is operated by displacing it in a longitudinal direction of the actuation mechanism. Further a dose setting mechanism may be rotatably arranged for setting a dose, wherein the dose setting mechanism may comprise a generally tubular activator sleeve provided with a spirally extending groove on its outer surface.

Favourably the groove is arranged with a length corresponding to the total amount of medicament to be delivered in a number of doses contained in the medicament container. Also, the groove may be provided with an end wall. A stop ring may be arranged coaxial with the activator sleeve, wherein the activator sleeve may be arranged with a follower positioned in the groove, wherein the follower is arranged to abut the end wall of the groove when the total amount has been delivered.

With this solution, it is ascertained that no dose larger than the remaining dose of the medicament container can be set or delivered. This is important because a user could otherwise get the impression that a full dose has been given since he/she was able to set a dose before delivery.

According to one solution, the stop ring may be arranged non-rotatable but movable in a longitudinal direction of the module. It is then thus moved in the longitudinal direction each time the activator sleeve is rotated due to the spirally extending groove.

Further, in order to be able to set a dose of medicament, the dose setting mechanism may preferably comprise a grip part arranged releasably connected to activator sleeve. It is then easy for a user to operate the grip part in order to set a dose. The grip part is preferably releasable and in particular after a dose has been set and a dose is to be delivered. This is because the activator sleeve is turning also during dose delivery and it is not desirable that the grip part is rotating at that stage.

As stated above, the activator sleeve rotates somewhat also during dose delivery, i.e. when the actuator is manually pressed in the proximal direction. The rotation of the activator sleeve has the feature of locking the activator in a depressed state after completed dose delivery. Because of this, the activator sleeve may comprise protrusions arranged to interact with the actuator such that activator sleeve is rotated when the actuator is operated. The protrusions of the activator sleeve then cooperate with ledges of the actuator, which ledges are arranged inclined in relation to the longitudinal direction.

As stated above, the actuator is locked after dose delivery and this may be performed in that the actuator is arranged with locking elements arranged to cooperate with the protrusions of the activator sleeve such as to lock the actuator after operation for delivering a dose of medicament. The locking elements may comprise ledges arranged generally transversal to said longitudinal direction. The locking elements may also comprise ramped or wedge-shaped sections on which the protrusions of the activator sleeve may slide before coming in contact with the generally transversal ledges.

In order to provide a subsequent operation of the actuation mechanism, the transversal ledges may be interconnected with the inclined ledges such that turning of the activator sleeve moves the protrusions from a locking position to a release position of the actuator. According to a further aspect, the actuation mechanism may further comprise a drive member acting on the actuator for urging it in a distal direction of the actuation mechanism when the actuator is released.

In addition, the actuation mechanism may further comprise a toggle sleeve operably arranged between the actuator and the plunger rod for urging the plunger rod in a proximal direction during operation of the actuator. In this respect, the plunger rod may be arranged with threads, a driver non-rotatably connected to the plunger rod, which driver is arranged with protrusions on its outer surface, that the toggle sleeve is arranged with surfaces inclined in relation to the longitudinal direction, causing a rotation of the plunger rod when the actuator and the toggle sleeve are moved in the proximal direction.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 2 is a cross-sectional view of the medicament delivery device of FIG. 1, FIG. 3 is a detailed view of a medicament container fastener of the device of FIG. 1, FIG. 12 is a detailed view with housing parts removed showing a different functional stage of the medicament delivery device, FIG. 13 is a detailed view with housing parts removed showing a different functional stage of the medicament delivery device, FIG. 14 is a detailed view with housing parts removed showing a different functional stage of the medicament delivery device, FIG. 15 is a detailed view with housing parts removed showing a different functional stage of the medicament delivery device, FIG. 16 is a detailed view with housing parts removed showing a different functional stage of the medicament delivery device, FIG. 18 is a detailed view with housing parts removed showing a different functional stage of the medicament delivery device, FIG. 19 is a detailed view with housing parts removed showing a different functional stage of the medicament delivery device, FIG. 22 is a detailed view with housing parts removed showing a different functional stage of the medicament delivery device, and FIG. 23 is a detailed view with housing parts removed showing a different functional stage of the medicament delivery device.

DETAILED DESCRIPTION

Figure 1:
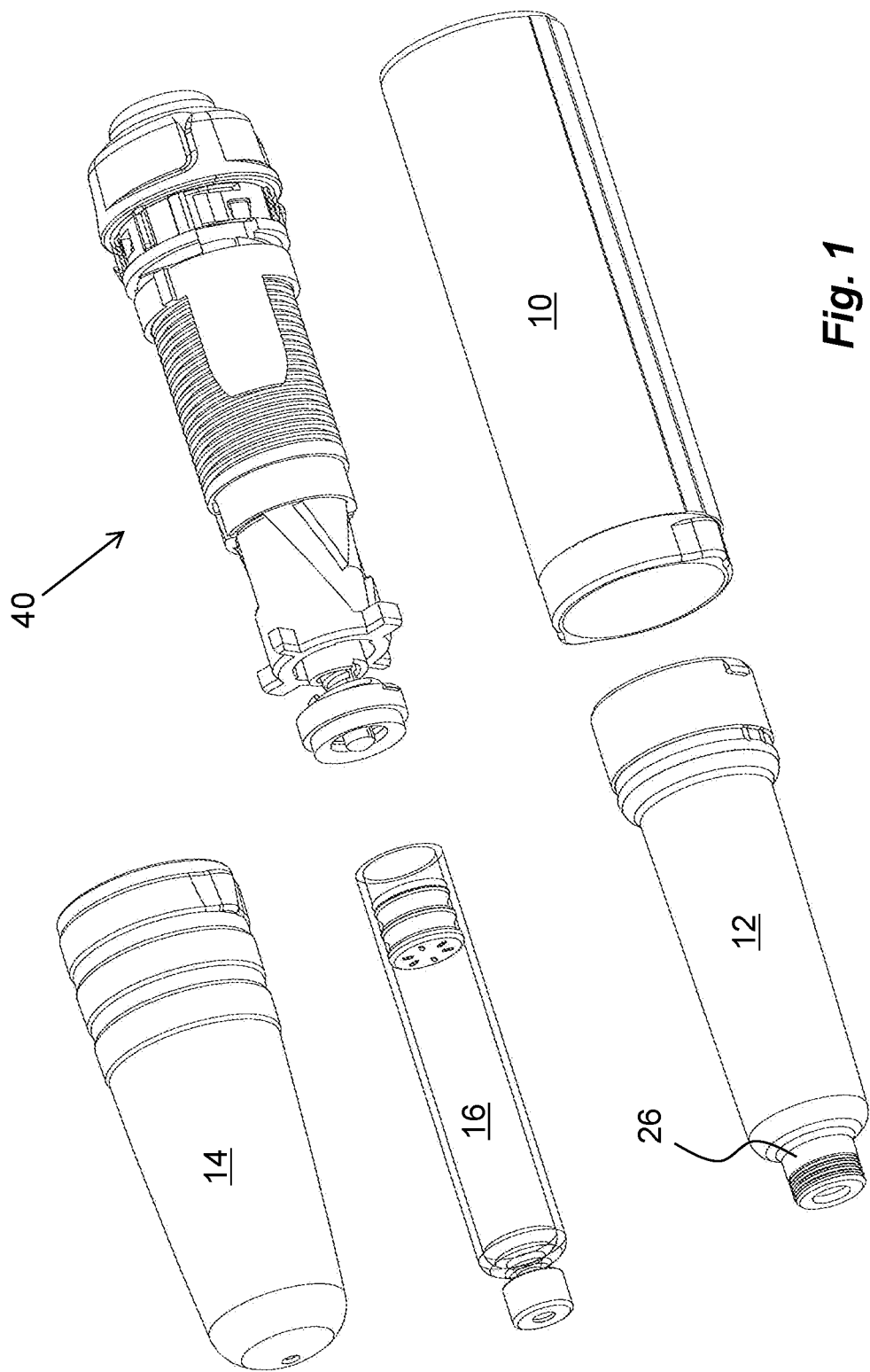
FIG. 1 is an exploded view of a medicament delivery device comprising a drive mechanism according to the present disclosure.

In the embodiment shown in the drawings, the medicament delivery device comprises a generally tubular distal housing part 10 and a generally tubular proximal housing part 12. In this regard it is to be understood that the housing may comprise a number of different sub-parts depending on manufacturing and assembly aspects. The proximal end of the distal housing part is arranged with attachment elements such that proximal housing part 12 can be attached. Thereby the distal end of the proximal housing part 12 is arranged with a central passage having a diameter generally corresponding to the diameter of the proximal end of the distal housing part 10 and provided with corresponding attachment elements. In this regard it is to be understood that the attachment elements may have a number of different shapes and functions for attaching the medicament container holder to the housing, such as threads, bayonet couplings, snap-in protrusions etc., if the proximal housing part 12 is to be releasably attached to the distal housing part 10. If the proximal housing part 12 is to be permanently attached, the attachment elements may comprise wedge-shaped grip protrusions and recesses that allow assembly but prevent disassembly, welding, glue, etc. A protective cap 14 is also provided for releasably covering the proximal housing part 12.

The proximal housing part 12 is designed as a medicament container holder and is arranged to house a generally tubular elongated medicament container 16, which is provided with a resilient movable stopper 18. The proximal housing part 12 may be transparent or may be provided with openings or windows so that the medicament container 16 and its content may be viewed. The proximal end of the medicament container 16 is provided with a neck portion 22 arranged with a penetrable septum 24, FIG. 2. The neck portion 22 is arranged to fit into a neck portion 26 of the proximal housing part 12. The neck portion 26 of the proximal housing part 12 is provided with attachment elements for a medicament delivery member that may be an injection needle provided with a hub having corresponding attachment elements. In this regard the attachment elements may be threads, bayonet couplings, snap-in attachments, luer-connections, just to mention a few options. Further, a generally ring-shaped medicament container fastener 30 is arranged to abut a distally directed surface of a medicament container 16 placed in the proximal housing part 12 with a proximally directed surface. The medicament container fastener 30 is urged in the proximal direction by a compression spring 31 arranged between the medicament container fastener 30 and a proximally directed surface of an end wall 32 of the distal housing part 10. The movement in the proximal direction of the medicament container fastener 30 is limited by radially outwardly directed protrusions 34 on an outer surface of the medicament container fastener 30 cooperating with cut-outs 36 of proximally directed ledges 38 on the proximally directed surface of the end wall 32, FIG. 4.

Figure 4:
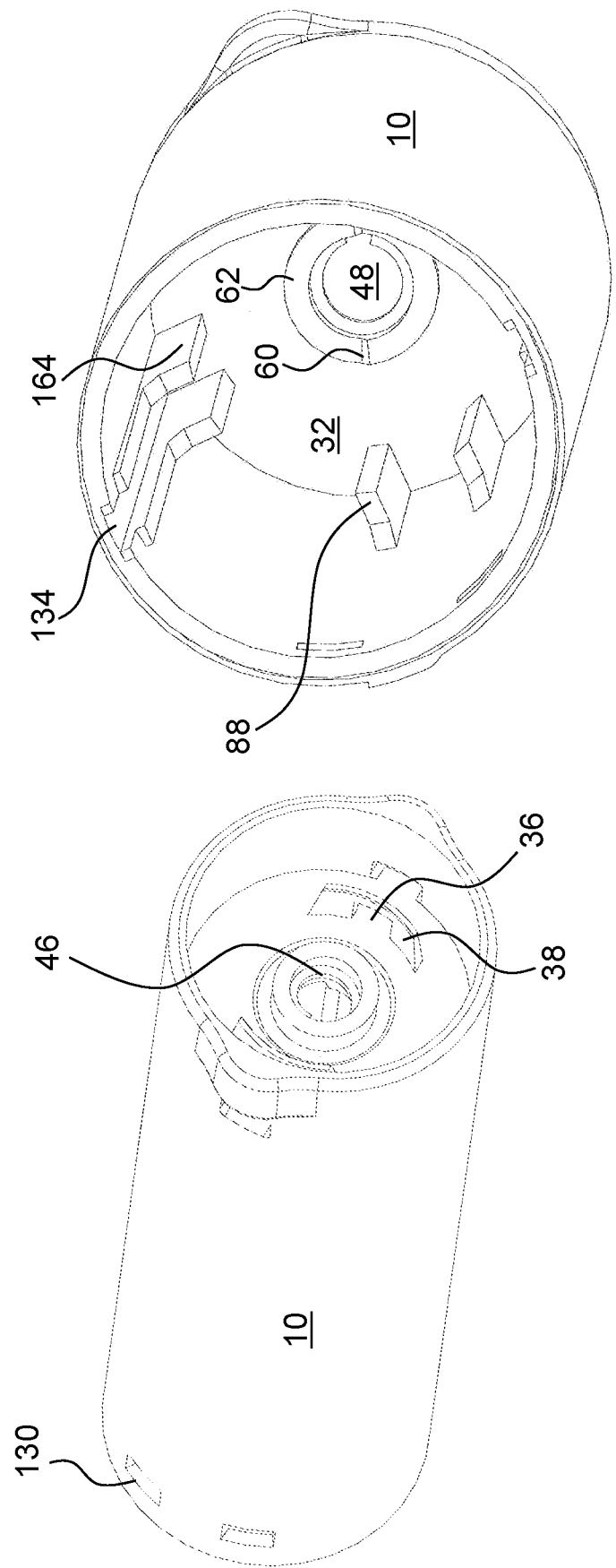
FIG. 4 is detailed views of components comprised in the medicament delivery device of FIG. 1.
Figure 5:
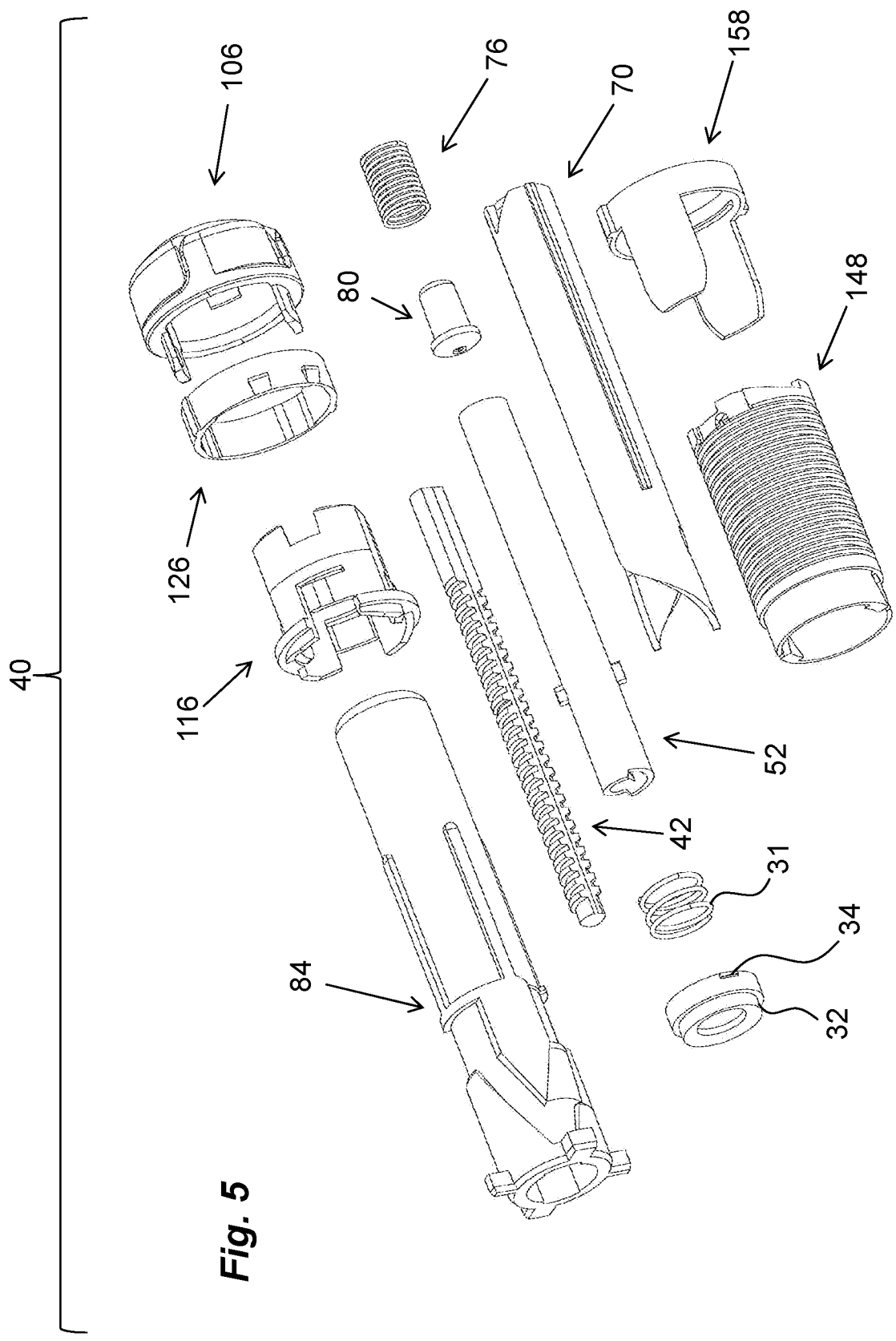
FIG. 5 is an exploded view of a drive mechanism according to the present disclosure.
Figure 6:
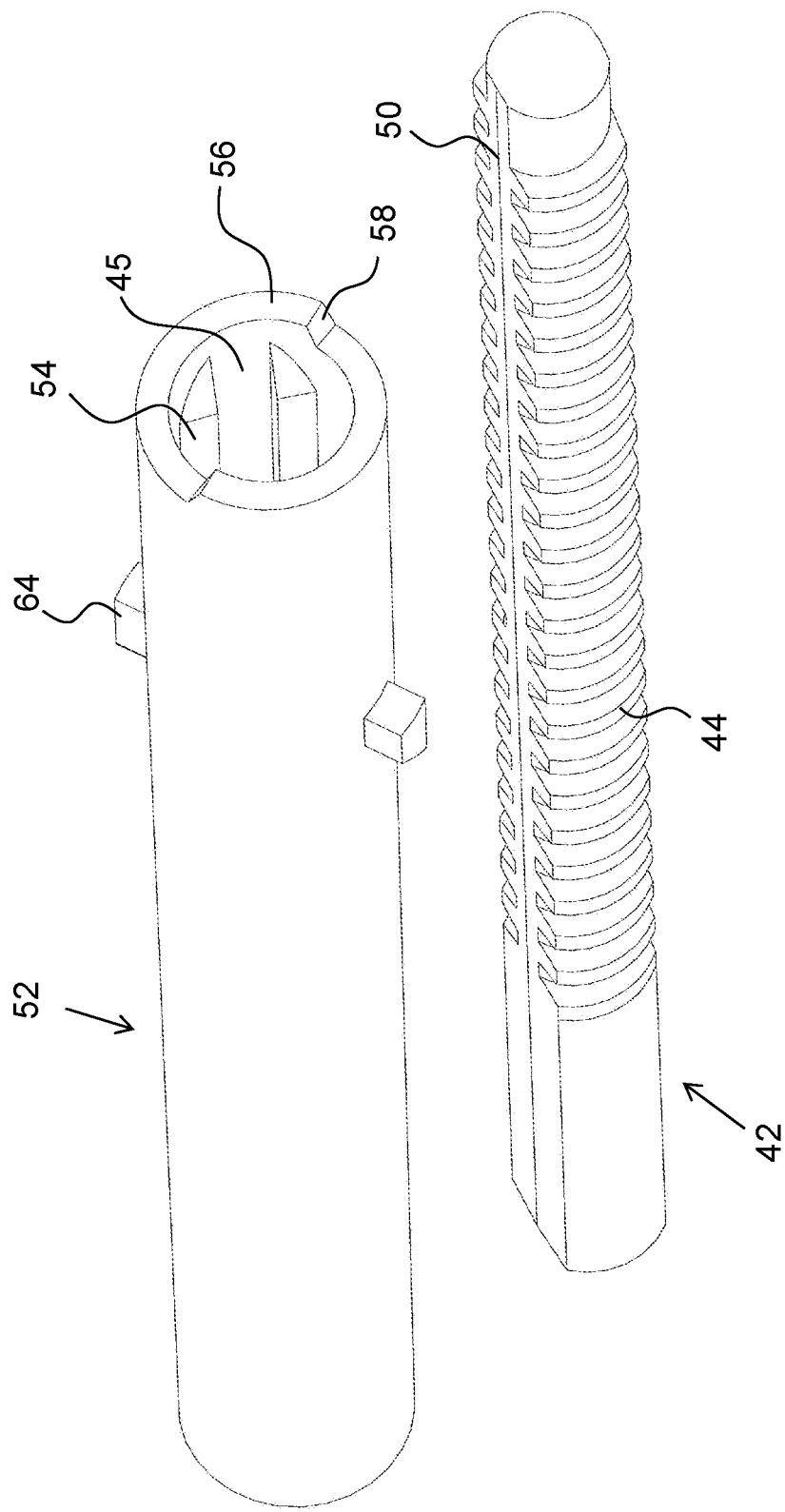
FIG. 6 is a detailed view of components comprised in the medicament delivery device of FIG. 1.

The medicament delivery device further comprises an actuation mechanism 40, FIGS. 1 and 5. The actuation mechanism 40 comprises an elongated plunger rod 42, FIGS. 5 and 6, provided with threads 44 on its outer surface, which threads 44 are arranged to cooperate with corresponding thread segments 46 in a central passage 48 in the proximal end wall 32 of the distal housing part 10, FIG. 4. The plunger rod 42 is arranged with two longitudinally cut-away sections 50, on opposite sides of the plunger rod 42, forming support surfaces. The plunger rod 42 is arranged to fit into a generally tubular driver 52. The inner surface of the driver 52 is arranged with two sets of longitudinally extending ledges 54 wherein the plunger rod 42 fits into the space 45 between these sets of ledges 54 such that the support surfaces of the cut-away sections 50 of the plunger rod 42 will be in contact with side surfaces of the ledges 54, whereby the plunger rod 42 is rotationally locked to the driver 52 but linearly movable in the longitudinal direction. The proximal end of the driver 52 is provided with ramped surfaces 56 that end in ledges 58, which ledges 58 interact with ledges 60 on ramped surfaces 62 on a distally directed surface of the end wall 32 of the distal housing part 10 surrounding the threaded central passage 48.

Figure 7:
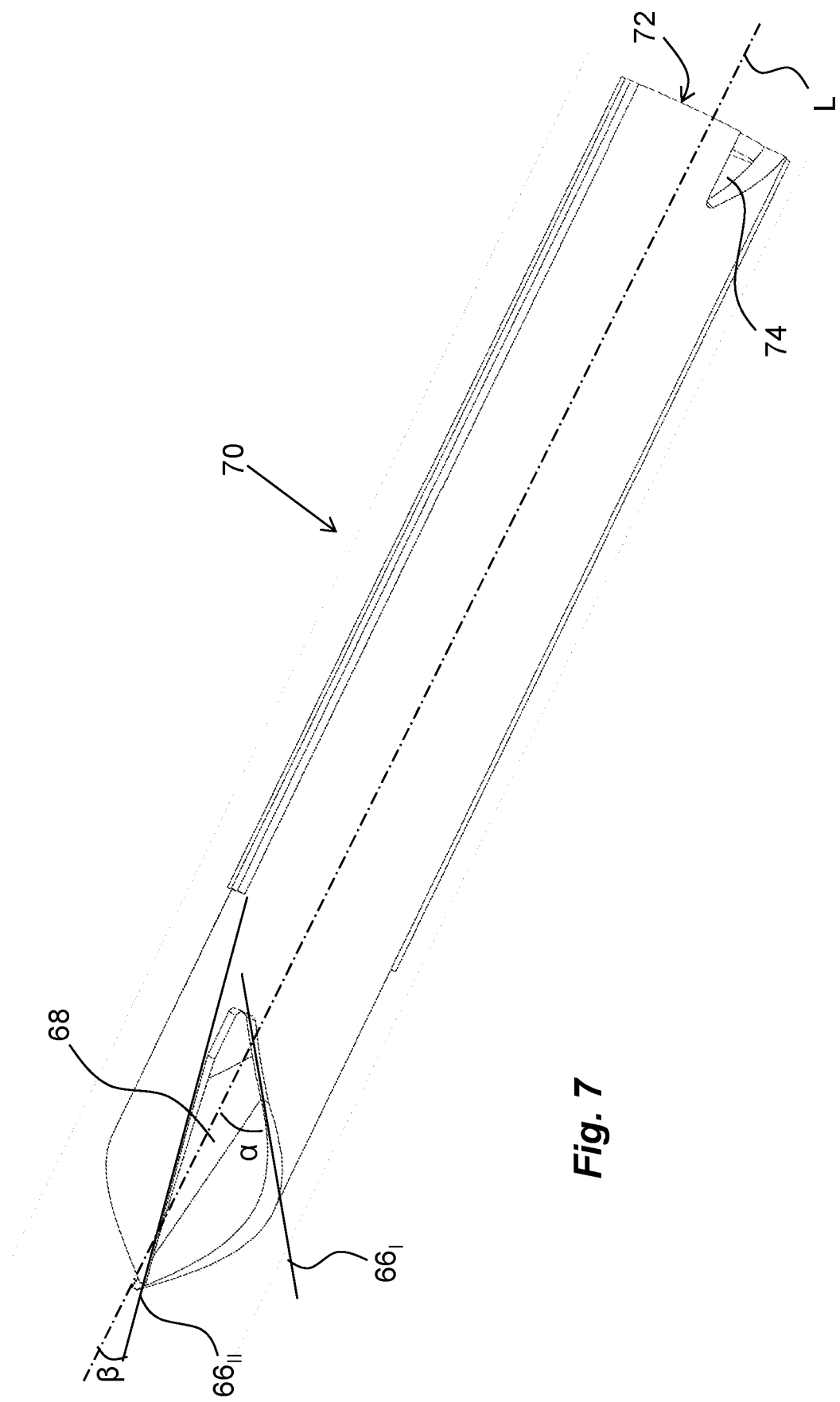
FIG. 7 is a detailed view of components comprised in the medicament delivery device of FIG. 1.

The outer surface of the driver 52 is further arranged with two outwardly directed protrusions 64 arranged on opposite sides of the driver 52, FIG. 6. These protrusions 64 are arranged to interact with edge surfaces 66 of cut-outs 68 at a proximal part of a generally tubular toggle sleeve 70, which is positioned coaxial and outside the driver 52. The edge surfaces 66 of the toggle sleeve 70 have a certain configuration as seen in FIG. 7, having a first section $66_I$ with an inclination alpha. The first section $66_I$ is then interrupted by a second section $66_{II}$ with a very steep inclination beta and in an opposite direction as the first section $66_I$. The second section $66_{II}$ then ends in a further first section $66_I$. The first and second sections are arranged twice around the proximal end of the toggle sleeve 70. The function of the protrusions 64 and the edge surfaces 66 will be described in detail below. The toggle sleeve 70 is further arranged with an end wall 72 at its distal end and wedge-shaped cut-outs 74 on a distal end area of the toggle sleeve 70, the function of which will be described below. A compression spring 76, hereafter named toggle sleeve spring, FIGS. 3 and 5, is arranged with a distal end in contact with a proximal surface of the end wall 72 of the toggle sleeve 70, and with a proximal end in contact with distally directed surface of an annular flange 78 of a generally tubular washer 80, FIG. 2, wherein the washer body extends into the toggle sleeve spring 76. A proximally directed surface of the flange 78 of the washer 80 is in contact with a distal end surface 82 of the driver 52.

Figure 8:
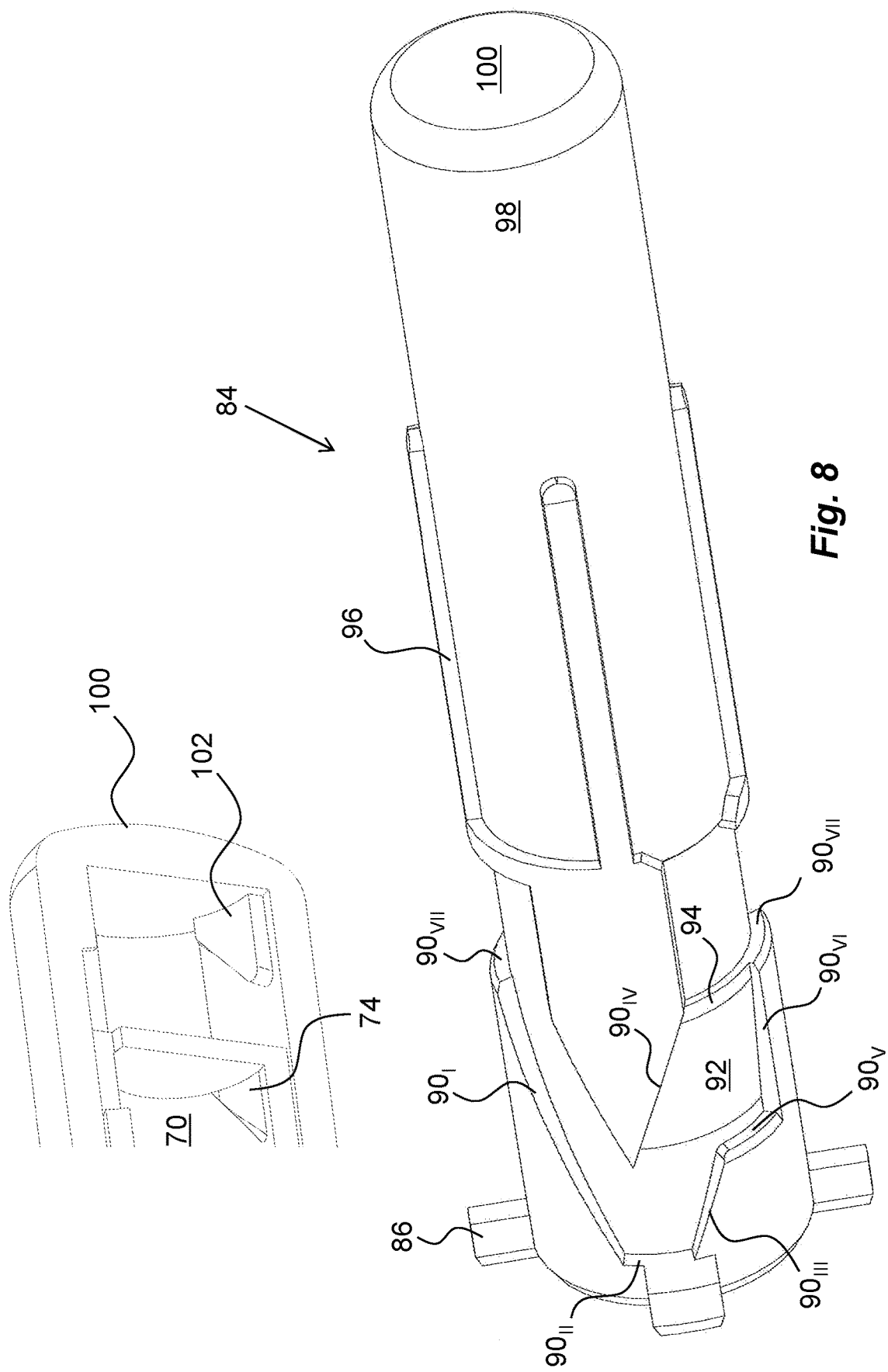
FIG. 8 is a detailed view of components comprised in the medicament delivery device of FIG. 1.

Coaxial with and outside of the toggle sleeve 70 is a generally tubular actuator 84, FIG. 8. The actuator 84 is arranged with a number of radially outwardly directed ledges 86 at a proximal part thereof, which ledges 86 are configured to fit in between pairs of longitudinally extending ledges 88, FIG. 4, on an inner surface of the distal housing part 10, thereby creating a rotational lock between the actuator 84 and the distal housing part 10 but allowing axial movement of the actuator 84. The actuator 84 is further arranged with a number of sets of ledges 90 on its outer surface, which ledges 90 have a certain extension as will be explained. A first section $90_I$ of the ledges is arranged facing the distal direction and with a steep inclination in relation to the longitudinal direction of the actuator 84. At one end of the first section, a second section $90_{II}$ is arranged, extending in the circumferential direction. A third section $90_{III}$ is connected to the second section $90_{II}$, extending with an inclination in relation to the longitudinal direction L. Parallel to the third section $90_{III}$, a fourth section $90_{IV}$ is placed, thus having an inclination in relation to the longitudinal direction L.

A fifth section $90_V$ then connects to the third section $90_{III}$, extending in the circumferential direction. The fifth section $90_V$ then connects to a sixth section $90_{VI}$ extending in the longitudinal direction. The sixth section $90_{VI}$ then connects to a seventh section $90_{VII}$ extending in the circumferential direction, which in turn connects to the first section of a subsequent set of sections 90. An area between the fourth section $90_{IV}$ and the sixth section $90_{VI}$ is arranged as a wedge-shaped ramp 92 having a distally directed ledge 94. The sets of ledges are repeated two times around the circumference of the actuator 84. Distally of the ledges 90 are a number of longitudinally extending ledges 96. The distal end part 98 of the actuator 84 is arranged with a somewhat dome-shaped end wall 100 wherein the distal end part 98 of the actuator 84 is arranged to protrude out of the distal end of the medicament delivery device and to act as a push button for a user, as will be described. A proximal surface of the end wall 100 is further arranged with proximally directed wedge-shaped protrusions 102, which protrusions 102 are arranged to cooperate with the wedge-shaped cut-outs 74 on the toggle sleeve 70, FIG. 8.

Figure 9:
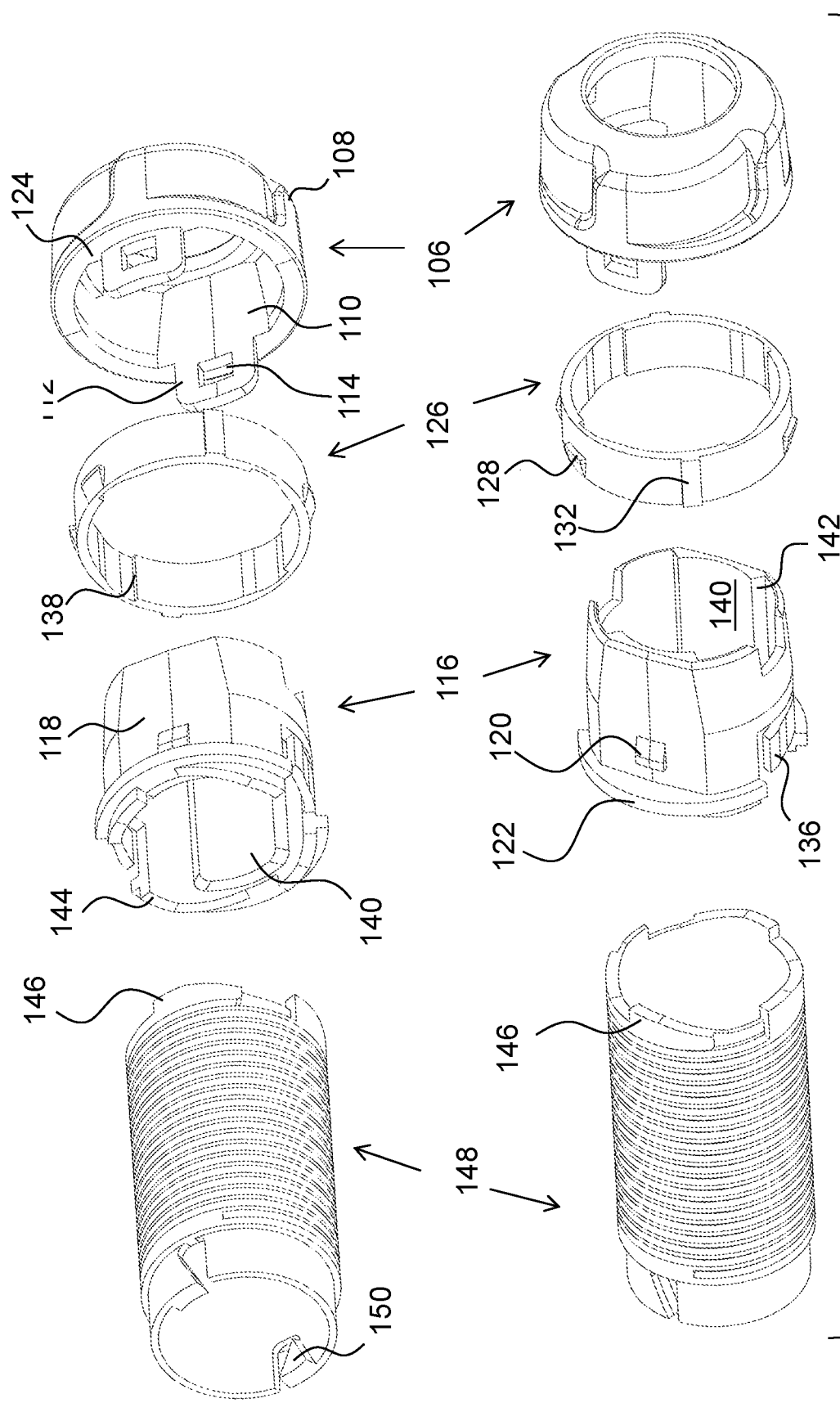
FIG. 9 is a detailed view of components comprised in the medicament delivery device of FIG. 1.

At the distal end of the housing a generally tubular activator 104 is arranged, FIG. 9. It has a distal grip part 106 that when connected to the distal housing part 10 is placed distally of the distal housing part 10 and having a diameter somewhat larger than the diameter of the distal housing part 10. The side surfaces of the grip part 106 may be arranged with grip elements, such as longitudinally extending ridges 108. The grip part 106 is further arranged with two planar surfaces 110 directed inwards and towards each other in the radial direction. Two proximally directed tongues 112 extend from the planar surfaces 110. The tongues 112 are arranged with cut-outs 114. The grip part 106 is arranged to fit onto a distal area of a generally tubular proximal part 116 of the activator 104 wherein the planar surfaces 110 of the grip part 106 are abutting corresponding planar surfaces 118 of the proximal part 116 that are facing radially outwards. The planar surfaces 118 of the proximal part 116 are arranged with wedge-shaped protrusions 120 that are intended to fit into the cut-outs 114 of the tongues 112 and lock the grip part 106 to the proximal part 116 when the two parts are assembled.

The proximal tubular part 116 of the activator 104 is arranged with an outwardly, circumferentially extending, ledge 122 in a proximal area thereof. Further, the grip part 106 is arranged with a proximally directed edge 124 such that when the grip part 106 is assembled with the proximal part 116, an annular recess is formed between the ledge 122 and the edge 124. A locking ring 126 is positioned rotationally in the recess between the ledge 122 and the grip part 106. The locking ring 126 is arranged with protrusions 128 on its outer surface, which protrusions 128 are arranged to fit into recesses 130, FIG. 4, on an inner surface of the distal housing part 10. Further, the outer surface of the locking ring 126 is arranged with ledges 132, which ledges 132 fit into longitudinally extending recesses 134 on the inner surface of the distal housing part 10, FIG. 4. This locks the activator 104 to the distal housing part 10, allowing rotation of the activator 104, as will be described.

Further, the proximal part 116 of the activator 104 is provided with a number of resilient arms 136 that extend in the circumferential direction of the activator 104. The arms 136 have a resiliency in the radial direction. The free ends of the arms 136 of the activator 104 are designed to be in contact with an inner surface of the locking ring 126 so as to cause a frictional resistance so as to avoid unwanted spontaneous movement of the activator 104 if the medicament delivery device for example is shaken. Further, the inner surface of the locking ring 126 is arranged with ledges 138 having surfaces in the circumferential direction, which ledges 138 cooperate with the free ends of the arms 136 so that the activator 104 can only be turned in one direction. Also, the inner surface of the proximal part 116 is arranged with two curved surfaces 140 provided at opposite sides and facing each other, having a curvature generally corresponding to the outer surface of the actuator 84. The curved surfaces are limited in the circumferential direction by longitudinally extending guide ledges 142, the function of which will be described below.

Further, at the proximally directed end surface of the activator 104, a number of proximally directed wedge-shaped protrusions 144 are arranged. These wedge-shaped protrusions 144 are designed to interact with at least one corresponding wedge-shaped protrusion 146 on a distal end surface of a generally tubular activator sleeve 148, FIGS. 9 and 10, which activator sleeve 148 is arranged rotational and slidable inside the distal housing part 10 and coaxial and outside the actuator 84. The inner surface of the activator sleeve 148 is arranged with two inwardly directed protrusions 150 at a proximal area thereof, which protrusions 150 are designed with a number of side surfaces having different inclinations as seen in FIG. 9. The protrusions 150 are designed to be in contact with and follow the ledges 90 of the actuator 84 as will be described. Adjacent the protrusions 150, cut-outs 151 are provided, enabling some flexing in the radial direction of the protrusions 150.

Figure 10:
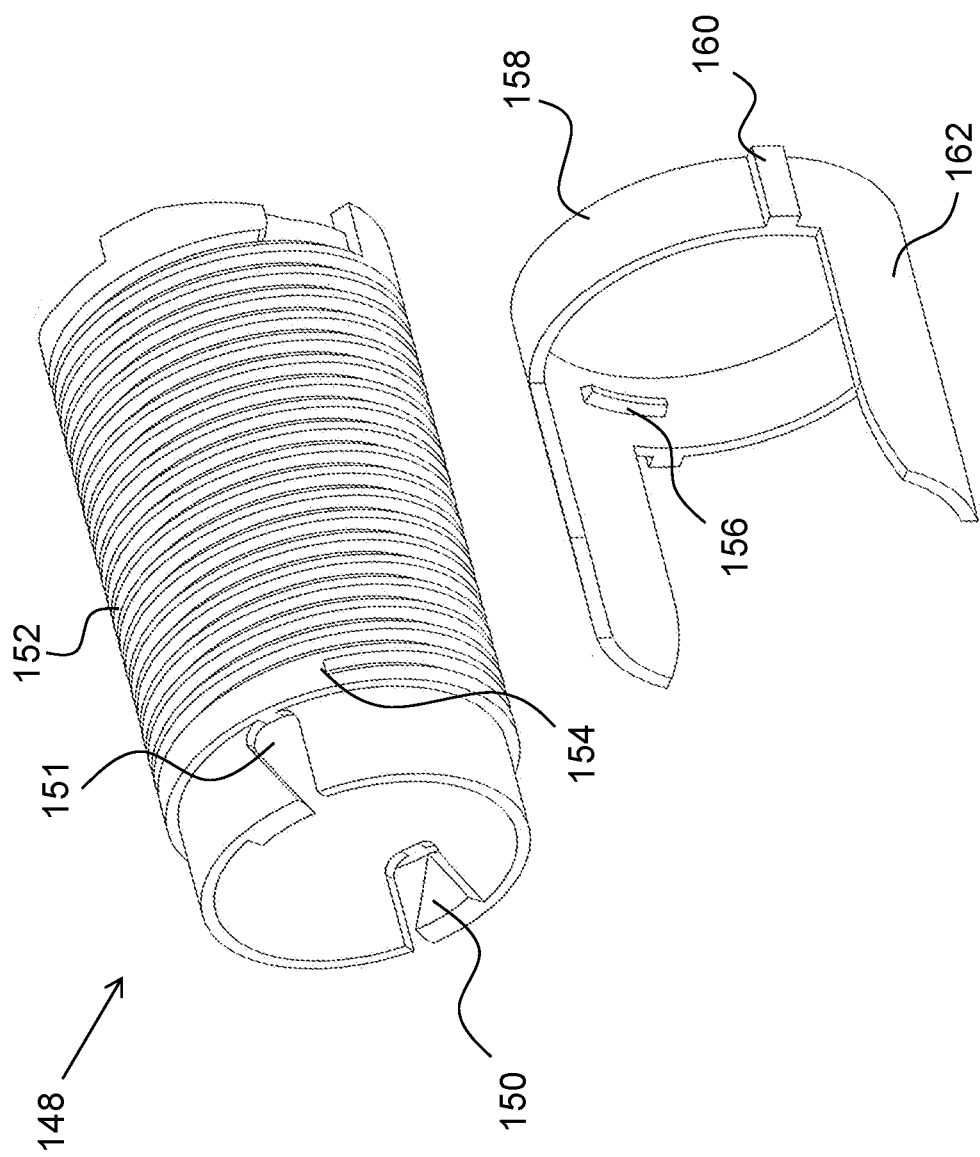
FIG. 10 is a detailed view of components comprised in the medicament delivery device of FIG. 1.

The activator sleeve 148 is further arranged with a spirally extending groove 152 on its outer surface, FIG. 10. The groove 152 has an end wall 154 at the proximal end of the activator sleeve 148. The groove 152 is intended to interact with at least one ledge 156 arranged on an inner surface of a stop ring 158, which stop ring 158 is positioned coaxially outside the activator sleeve 148. The outer surface of the stop ring 158 is arranged with longitudinally extending ledges 160, which ledges 160 are designed to fit into the longitudinally extending recesses 134 on the inner surface of the distal housing part 10 as seen in FIG. 4. This connection provides a rotational lock of the stop ring 158 while allowing movement in the longitudinal direction. The stop ring 158 is further arranged with proximally directed tongues 162, which tongues 162 are arranged to cooperate with ledges 164 on either side of the recesses 134 for providing guiding stability of the stop ring 158 as will be described.

The disclosure is intended to function as follows. When the device is delivered to a user, the plunger rod 42 is in its most distal position as shown in FIG. 2. Further the actuator 84 is in its most proximal position, with only a short part of the distal push button part 98 extending through the distal end of the medicament delivery device. The actuator 84 is locked in that position by the protrusions 150 of the activator sleeve 148 being in contact with the distal surface of the ledge $90_{VII}$ of the actuator, FIG. 11. This prevents movement of the actuator 84 in the distal direction against the urging force of the toggle sleeve spring 76 that is tensioned between the toggle sleeve 70 and the actuator 84. The activator 104 is in an initial position where the ends of the resilient arms 136 of the proximal part 116 are resting against the ledges 138 of the wedge-shaped protrusions on the inner surface of the locking ring 126.

The medicament delivery device could either be delivered to a user with a medicament container 16 already mounted in the proximal housing part 12 and thus ready to use or be delivered without a medicament container mounted and possibly also with the proximal housing part 12 unconnected to the distal housing part 10, wherein the user has to put a medicament container 16 inside the proximal housing part 12 and then attach the proximal housing part 12 to the distal housing part 10 of the medicament delivery device. The container fastener 30 with the spring 31 is now pressing the medicament container in the proximal direction, thereby reducing the risk of rattling of the medicament container.

In either way, when the medicament delivery device is to be used, the protective cap 14 is removed and a medicament delivery member is attached to the neck portion 26 of the proximal housing part 12. When the medicament delivery member is an injection needle, the attachment causes a distal pointed end of the injection needle to penetrate the septum 24 of the medicament container, thereby causing a flow passage through the needle from the interior of the medicament container 16.

In order to unlock and activate the medicament delivery device, the user turns the grip part 106, which is counter clockwise in the embodiment shown. Any rotation in the opposite direction is prevented by the arms 136 of the proximal part 116 engaging the ledges 138 of the wedge-shaped protrusions of the locking ring 126. In the embodiment shown, there are three ledges 138 of the wedge-shaped protrusions along the inner circumference of the locking ring 126 with thus a 120 degree displacement between the ledges 138, and consequently the activator 104 is turned 120 degrees per step, as will be described in more detail below.

Figure 11:
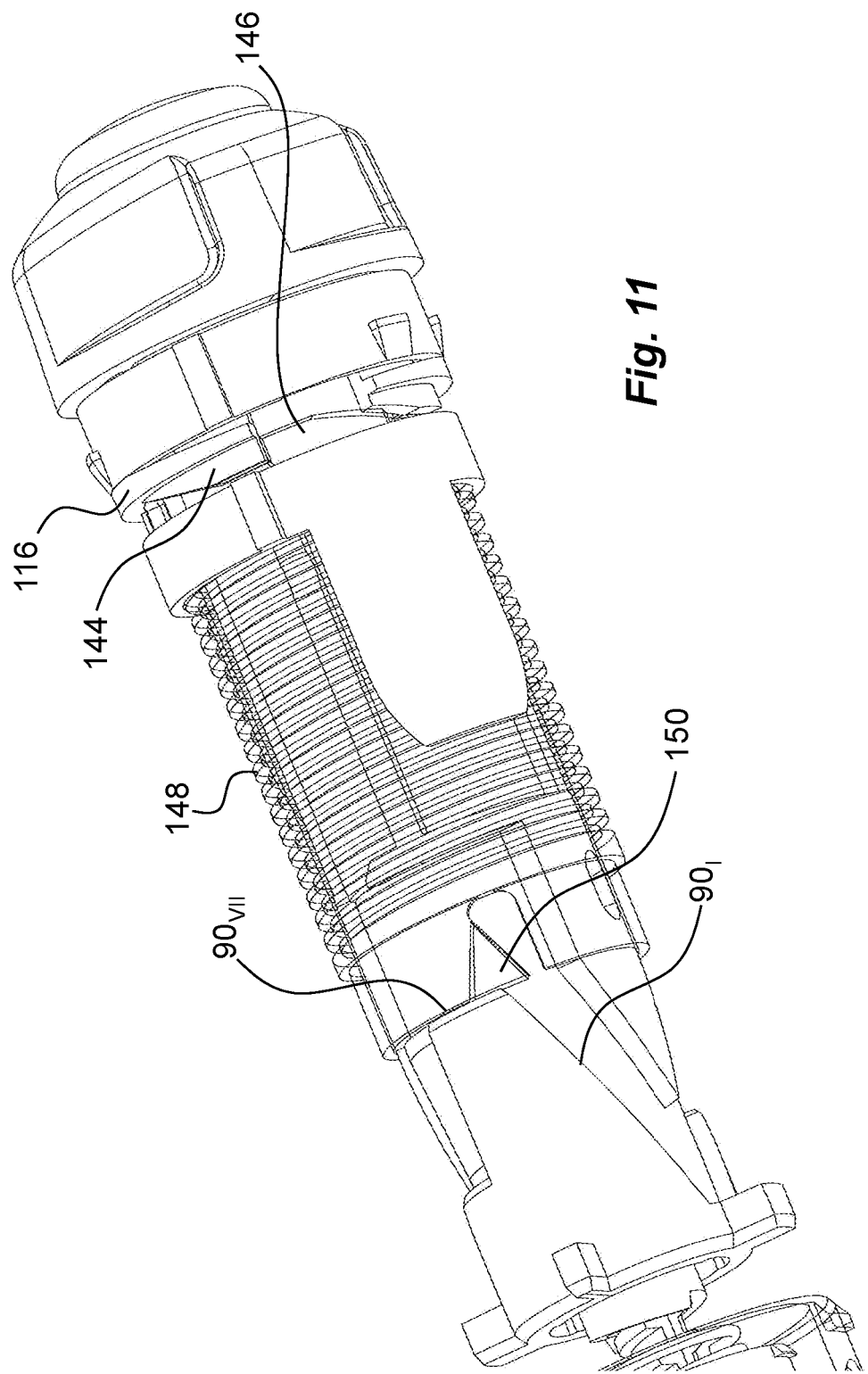
FIG. 11 is a detailed views with housing parts removed showing different functional stages of the medicament delivery device.

The initial mutual positions of the proximal part 116 and the activator sleeve 148 are shown in FIG. 11. In this position, the at least one wedge-shaped protrusion 144 of the proximal part 116 is in full contact with the space between the protrusions 146 of the activator sleeve 148, causing a rotational lock between the two components. When the grip part 106 with the proximal part 116 is turned, the activator sleeve 148 follows, whereby its protrusions 150 will slide along the ledge $90_{VII}$ of the actuator 84 until the protrusions 150 come to the steep ledge 90I, FIG. 11. This will enable the actuator 84 to be moved in the distal direction by the toggle sleeve spring 76 acting between the distal end of the driver 52 and the toggle sleeve 70, which in turn is abutting the distal end surface of the actuator 84, which in turn causes the push button part of the actuator 84 to extend in the distal direction through the distal end of the medicament delivery device. During the turning of the activator sleeve 148, the ledge 156 of the stop ring 158 will slide in the spiral groove 152 of the activator sleeve 148.

The user now stops turning the activator 104 but since the protrusions 150 of the activator sleeve is in contact with the steep inclined ledge 90I of the actuator 84, the activator sleeve 148 continues to rotate because the actuator 84 is rotationally locked to the housing by the ledges 86 cooperating with the ledges 88 of the distal housing part 10. When now the proximal part 116 is stationary and the activator sleeve 148 is rotating, the inclined surface of the at least one wedge-shaped protrusion 146 of the activator sleeve 148 will cooperate with the inclined surface of the wedge-shaped protrusions 144 of the proximal part 116, whereby the activator sleeve 148 is forced in the proximal direction. The rotation of the activator sleeve 148 is stopped when the protrusions 150 are moved in contact with the circumferential ledge 90II of the actuator 84, which stops the movement in the distal direction of the actuator 84, FIG. 12. The push button part 98 of the actuator 84 is protruding out of the distal end of the medicament delivery device as seen in FIG.

12. When the actuator 84 is moved in the distal direction, the ledges 96 on the outer surface of the actuator will be positioned parallel to the guide ledges 142 of the proximal part 116 of the activator 104, thereby preventing any turning of the activator 104.

When the actuator 84 is moving in the distal direction as described above, so is the toggle sleeve 70 since they are in contact with each other because the toggle spring is acting on the toggle sleeve 70, in turn acting on the actuator 84. In the initial position the protrusions 64 of the driver 52 are positioned in the junction between the first and second sections $66_I$ and $66_{II}$ of the edge surfaces 66 as seen in FIG. 13. When now the toggle sleeve 70 is moving in the distal direction together with the actuator 84 the protrusions 64 will slide along the first section $66_I$, FIG. 14, and because it has an inclination β in relation to the longitudinal direction, the toggle sleeve 70 will turn in relation to the driver 52. The driver 52 is prevented from turning in the anti-clockwise direction due to the ledges 58 of the driver 52 cooperating with the ledges 60 of the end wall 32 of the housing. The turning of the toggle sleeve 70 will cause it to move somewhat in the proximal direction in relation to the actuator 84 because of the cooperation between the ramped cut-outs 74 of the toggle sleeve 70 and the wedge-shaped protrusions 102 of the actuator 84, FIG. 15. During continued movement of the toggle sleeve 70 in the distal direction, the protrusions 64 of the driver 52 will come out of contact with the first section $66_I$ whereby the toggle sleeve 70 will be turned back to the initial position because of the cooperation between the ramped cut-outs 74 and the wedge-shaped protrusions 102 as seen in FIG. 16.

Figure 17:
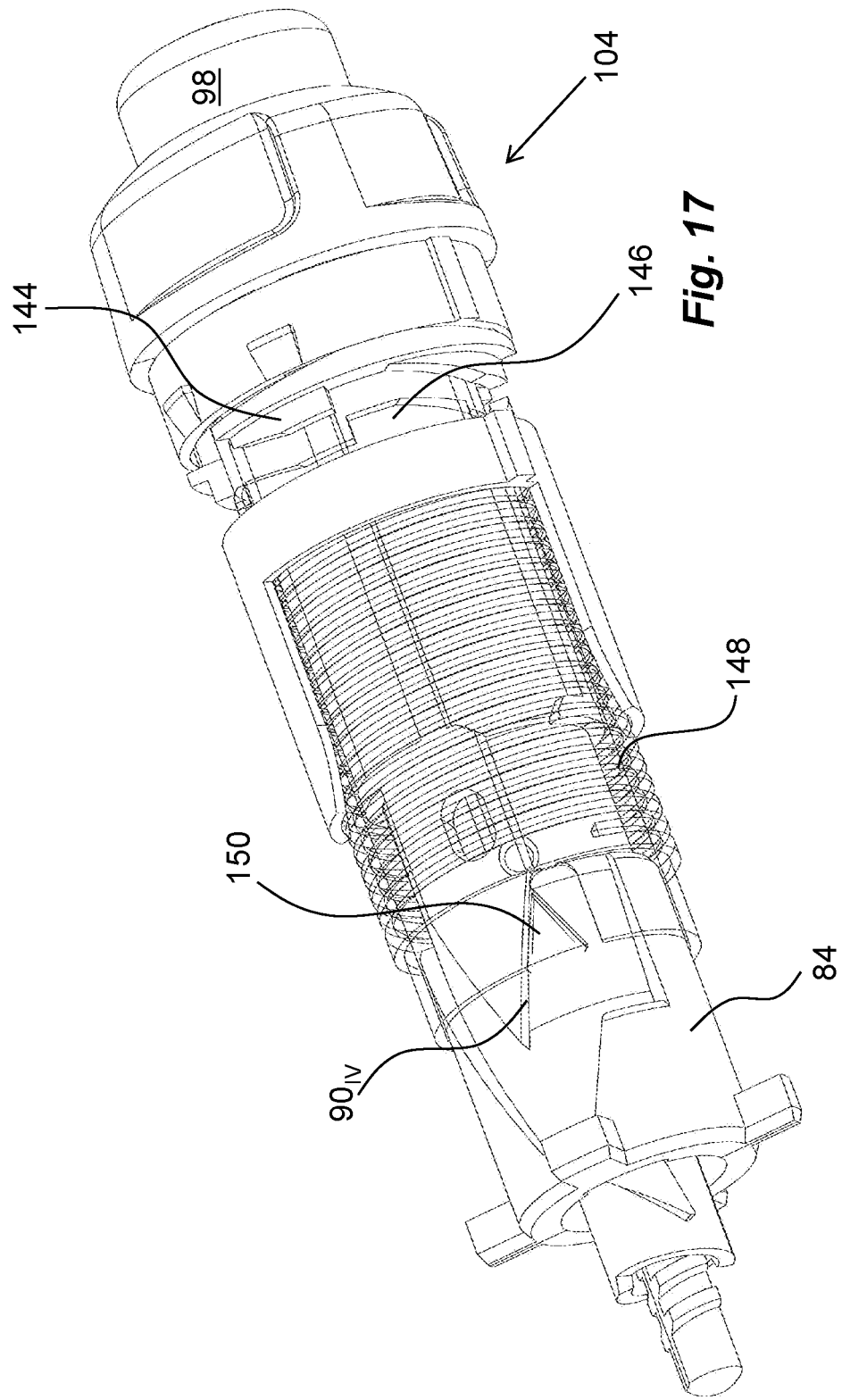
FIG. 17 is a detailed view with housing parts removed showing a different functional stage of the medicament delivery device.

The device is now activated and ready to deliver a dose of medicament. If a medicament delivery member has not been attached before, it may be attached now to the proximal end of the medicament delivery device. The proximal end of the medicament delivery device is now placed at a dose delivery site, and if the medicament delivery member is an injection needle, a penetration is performed at the dose delivery site. The next step is to deliver a dose of medicament. The user then presses on the push button part 98 of the actuator 84 so that it moves in the proximal direction. This will cause the inclined ledge $90_{IV}$ of the actuator 84 to be moved in contact with the protrusions 150 of the activator sleeve 148, FIG. 17. This will in turn move the activator sleeve 148 in the proximal direction whereby the wedge-shaped protrusions 146 of the activator sleeve 148 are moved out of contact with the wedge-shaped protrusions 144 of the proximal part. Any turning of the activator 104 will thus not affect the medicament delivery device. At the same time, the activator sleeve is turned due to the inclination of the ledge $90_{IV}$.

As the actuator 84 is moved in the proximal direction, so is the toggle sleeve 70. This movement will cause the first section $66_I$ of the cut-outs 68 to come in contact with the protrusions 64 of the driver, FIG. 18, and continuous movement of the toggle sleeve 70 will cause the protrusions 64 to slide along the inclined first section 60I, FIG. 19, whereby the driver 52 is turned in the clockwise direction. The turning is not obstructed by the ledges 56 of the driver 52 and the ledges 62 of the end wall 32 of the housing. The turning of the driver 52 will in turn cause a turning of the plunger rod 42 because of the rotational lock between them and since the plunger rod 42 is threadedly connected to the passage 48 of the end wall 32 of the housing 10, the plunger rod 42 will be moved in the proximal direction, FIG. 18, whereby it will act on the stopper 18 for expelling a dose of medicament through the medicament delivery member.

Figure 20:
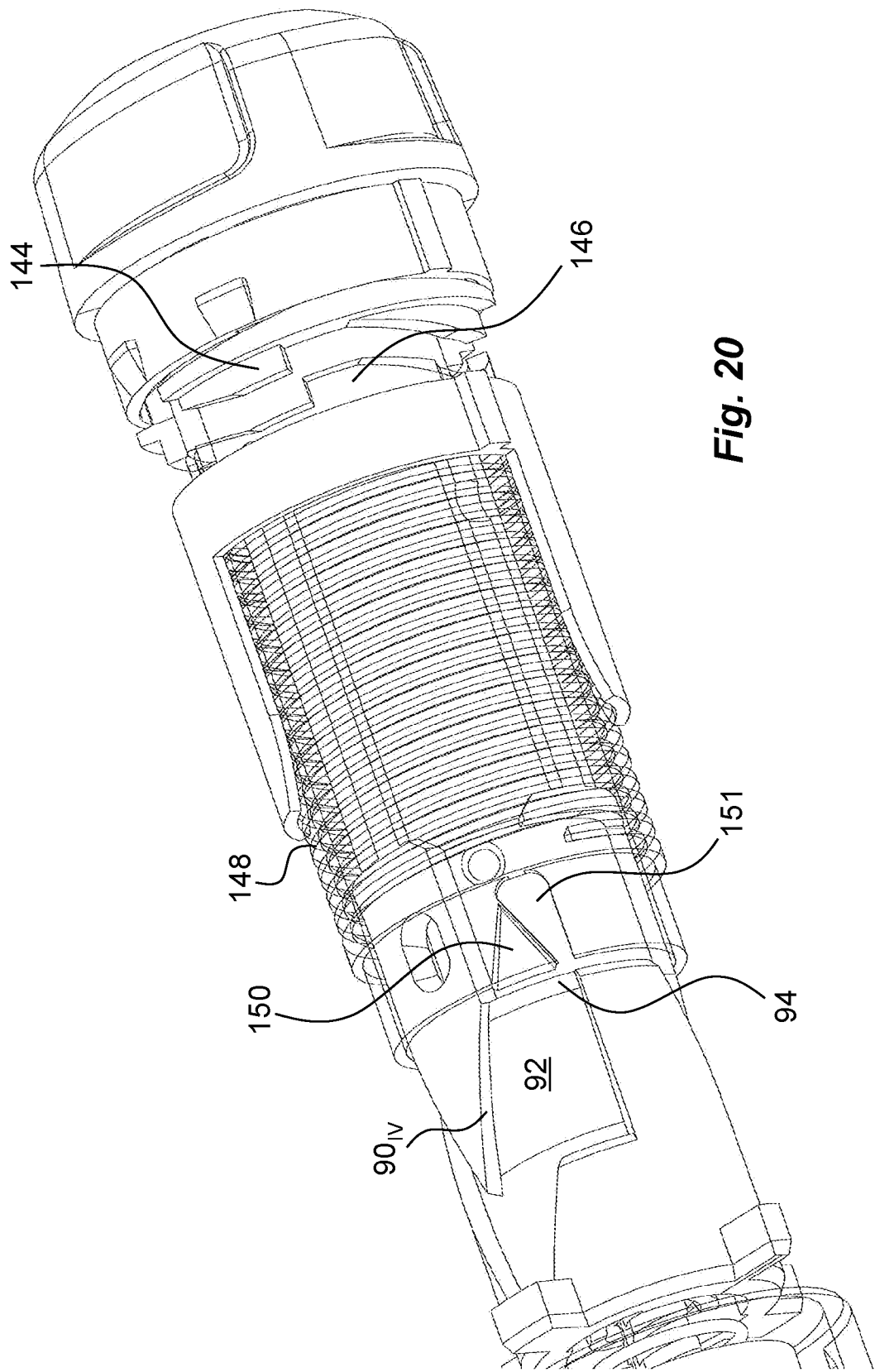
FIG. 20 is a detailed view with housing parts removed showing a different functional stage of the medicament delivery device.
Figure 21:
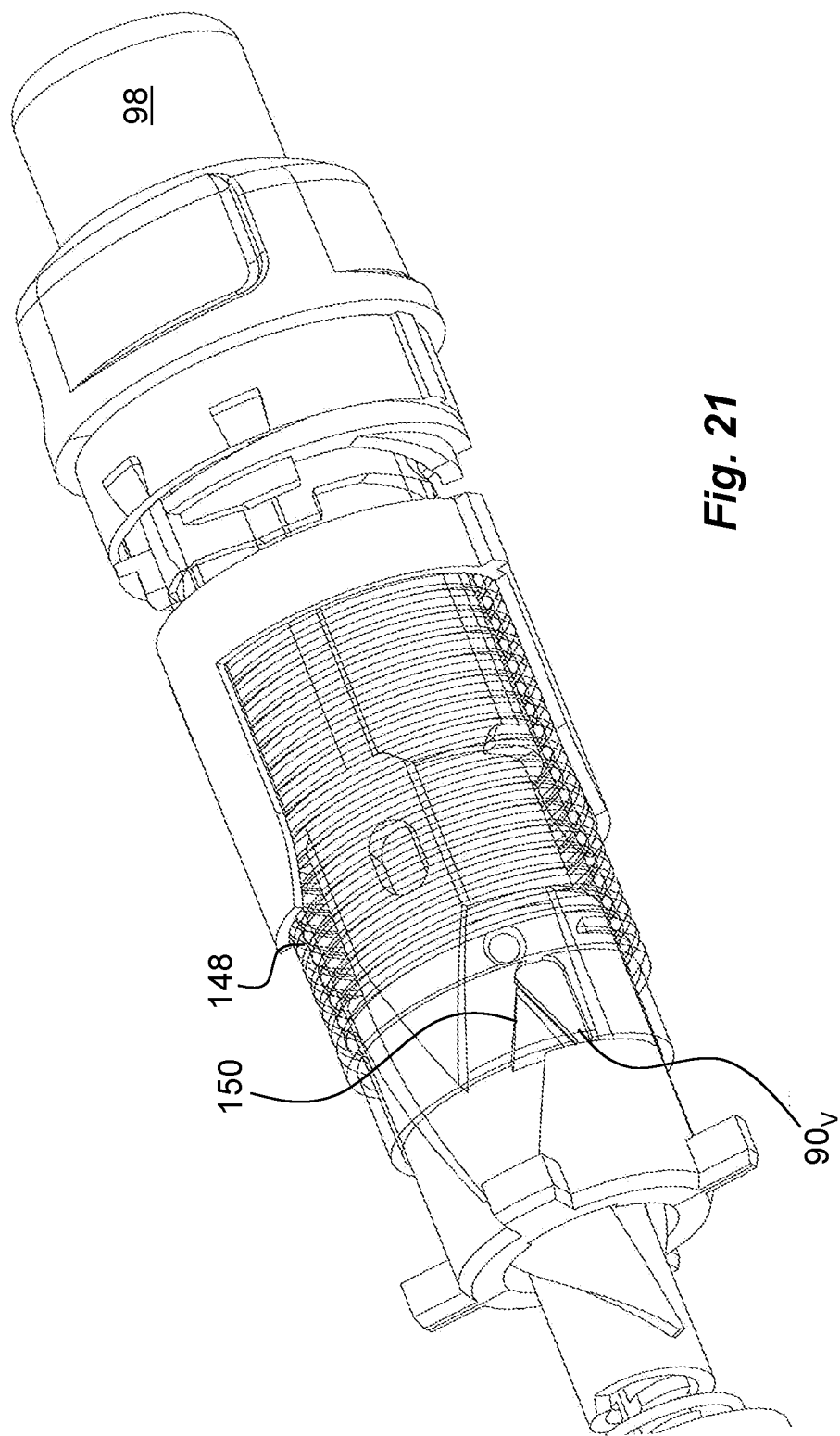
FIG. 21 is a detailed view with housing parts removed showing a different functional stage of the medicament delivery device.

During the movement in the proximal direction of the actuator, the protrusions 150 of the activator sleeve 148 will enter the ramped part and at the end of the movement of the actuator 84 pass the ledge 94, causing the actuator 84 to be locked in the depressed position, FIG. 20. The passing of the ledge 94 by the protrusions 150 is facilitated by the flex obtained by the cut-outs 151. There is further a safety feature, should the user during the pressing of the actuator 84 in the proximal direction suddenly release the actuator 84 before completing the dose delivery sequence. In this case only a part of the amount of medicament has been delivered. The toggle sleeve spring 76 will then try to force the actuator 84 in the distal direction. However, this is prevented in that the protrusion 150 will be moved in contact with the circumferentially extending ledge $90_V$, FIG. 21, thereby preventing further movement. If not stopped, it would otherwise lead to the actuator 84 being again moved to a fully extended position, whereby it would be possible to deliver a new full amount of medicament. This is now prevented by the ledge $90_V$. The user may now press on the partly extending push button part 98 for delivering the remainder of the dose of medicament, after which the actuator 84 is locked as described above.

The medicament delivery device may now be removed from the dose delivery site, the medicament delivery member removed and discarded in a safety container and the protective cap 14 re-connected to the proximal end of the medicament delivery device. The above mentioned sequences of dose setting and dose delivery are repeated until the medicament container 16 is empty and as described above, the ledge 156 of the stop ring 158 is moved a distance along the spiral groove 152 of the activator sleeve 148 for each dose setting operation, whereby the stop ring 158 is moved in the proximal direction. In order to prevent setting a dose that is larger than the remaining dose quantity of the medicament container, the length of the spiral groove 152 around the circumference of the activator sleeve 148 corresponds to the total amount of medicament in the medicament container. Thus, the setting of the last dose may be limited by the ledges 156 of the stop ring 158 abutting the end wall 154 of the groove 152, FIGS. 22 and 23, preventing further turning of the activator 104 and the activator sleeve 148. This means that no dose larger than the remaining amount of the medicament container 16 can be set.

It is to be understood that the embodiment described above and shown in the drawings is to be regarded only as a non-limiting example and that the disclosure may be modified in many ways within the scope of the patent claims.

We claim:

1. An actuation mechanism for use in a medicament delivery device, the actuation mechanism comprising:
   a plunger rod;
   an actuator slidably connected to the plunger rod that engages a stopper of a medicament container of the medicament delivery device when the actuator is operated by displacing the stopper in a longitudinal direction of the actuation mechanism;
   an activator rotatably arranged for activating the actuation mechanism and for setting a medicament dose, wherein the activator comprises a generally tubular activator sleeve, wherein the activator sleeve is arranged rotationally inside a generally tubular distal housing part of the medicament delivery device, wherein the activator sleeve includes protrusions arranged to interact with the actuator such that the activator sleeve is rotated when the actuator is operated, wherein the actuator is arranged with a plurality of inclined ledges cooperating with the protrusions, and wherein the plurality of inclined ledges are arranged inclined in varying angles of inclination in relation to the longitudinal direction; and a stop ring arranged coaxial with the activator sleeve and comprising an inwardly protruding ledge.

2. The actuation mechanism of claim 1, wherein the plunger rod is threaded.

3. The actuation mechanism of claim 1, wherein the activator sleeve includes a spirally extending groove on its outer surface.

4. The actuation mechanism of claim 3, wherein the groove has an end wall and a length corresponding to a total amount of medicament to be delivered in a number of doses contained in a medicament container.

5. The actuation mechanism of claim 4, wherein the inwardly protruding ledge of the stop ring is rotationally engaged within the groove such that activator sleeve rotates relative to the inwardly protruding ledge and the inwardly protruding ledge abuts the end wall when the total amount of medicament has been delivered.

6. The actuation mechanism of claim 1, wherein the plunger rod has a non-circular cross section.

7. The actuation mechanism of claim 1, further comprising a tubular driver rotationally fixed to the plunger rod.

8. The actuation mechanism of claim 1, wherein the stop ring is arranged non-rotatable but movable in the longitudinal direction of the actuation mechanism.

9. The actuation mechanism of claim 1, wherein the activator comprises a grip part arranged releasably connected to the activator sleeve.

10. The actuation mechanism of claim 1, wherein the actuator is arranged with locking elements arranged to cooperate with the protrusions of the activator sleeve to lock the actuator after operation for delivering a dose of medicament.

11. The actuation mechanism of claim 10, wherein the locking elements comprise transversal ledges arranged generally transversal to the longitudinal direction.

12. The actuation mechanism according to claim 11, wherein the transversal ledges are interconnected with the plurality of inclined ledges such that turning of the activator sleeve moves the protrusions from a locking position to a release position of the actuator.

13. The actuation mechanism according to claim 12, further comprising a drive member acting on the actuator for urging the actuator in a distal direction of the actuation mechanism when the actuator is released.

14. The actuation mechanism according to claim 13, further comprising a toggle sleeve operably arranged between the actuator and the plunger rod for urging the plunger rod in a proximal direction during operation of the actuator.

15. The actuation mechanism according to claim 14, wherein the plunger rod is arranged with threads, wherein a driver is non-rotatably connected to the plunger rod, wherein the driver is arranged with protrusions on its outer surface, wherein the toggle sleeve is arranged with surfaces inclined in relation to the longitudinal direction, causing a rotation of the plunger rod when the actuator and the toggle sleeve are moved in the proximal direction.

16. The actuation mechanism according to claim 1, wherein the activator sleeve is arranged slidable in the longitudinal direction inside the generally tubular distal housing part of the medicament delivery device.

17. A medicament delivery device, comprising:
a generally tubular distal housing part;
a generally tubular proximal housing part;
a medicament container positioned within the generally tubular proximal housing part; and
the actuation mechanism of claim 1 positioned within the generally tubular distal housing part.

18. The medicament delivery device of claim 17, further comprising a protective cap for releasably covering the generally tubular proximal housing part.

19. The medicament delivery device of claim 17, wherein the device is configured to deliver multiple doses from the medicament container.

20. The medicament delivery device of claim 17, wherein the device is configured to prevent a dose larger than the remaining dose of the medicament container from being set or delivered.

* * * * *